United States Patent [19]

Krzysik

[11] Patent Number: 5,330,747
[45] Date of Patent: Jul. 19, 1994

[54] COSMETICS WITH ENHANCED DURABILITY

[75] Inventor: Duane G. Krzysik, Midland, Mich.

[73] Assignee: Dow Corning Corporation, Midland, Mich.

[21] Appl. No.: 12,695

[22] Filed: Feb. 3, 1993

[51] Int. Cl.$^5$ .................. A61K 7/021; A61K 7/42
[52] U.S. Cl. .......................... 424/63; 424/59; 424/401; 424/DIG. 5
[58] Field of Search .............. 424/63, 401, DIG. 5

[56] References Cited

U.S. PATENT DOCUMENTS 5,118,507 6/1992 Clement ........................ 424/401
5,162,410 11/1992 Sweet ............................. 524/266

Primary Examiner—Thurman K. Page
Assistant Examiner—Jyothsna Venkat
Attorney, Agent, or Firm—James L. DeCesare

[57] ABSTRACT

A method of enhancing adherence to the skin or eyelash of a skin care preparation containing an active ingredient by incorporating into the skin care preparation a film forming agent as an ingredient, and applying the skin care preparation containing the active ingredient and the film forming agent to the skin. The improvement resides in the film forming agent being a silicone pressure sensitive adhesive. Sunscreen preparations and eye cosmetics are described.

2 Claims, No Drawings

COSMETICS WITH ENHANCED DURABILITY

BACKGROUND OF THE INVENTION

This invention is directed to personal care, and more particularly to skin care products including color cosmetics, which have been found to possess improved skin substantivity characteristics.

Water and wear resistance are vital properties to skin protection products, since contact with water by perspiration and swimming, can destroy the effectiveness of an otherwise beneficial skin care product. Where greater protective qualities, high water resistance, and substantive barrier characteristics, are desired in a skin care product, it is customary in the art to incorporate various organic waxes, organic resins, and organic polymers, into the skin care product in order to achieve these goals.

What has been discovered in accordance with the present invention is that certain silicone based materials can be employed as viable alternatives to the organic waxes, resins, and polymers, customarily used heretofore. Specifically, the silicone based material is a silicone pressure sensitive adhesive.

While the silicone pressure sensitive adhesive is described in U.S. Pat. No. 5,162,410 issued Nov. 10, 1992, which is incorporated herein by reference, the use of the adhesive of the U.S. Pat. No. 5,162,410 in the manner set forth in accordance with the present invention, has not been previously exploited. Thus, insofar as the U.S. Pat. No. 5,162,410 is concerned, the use of the adhesive therein is described with reference to transdermal drug delivery involving adherence of a drug containing patch to the skin.

There is no suggestion in the U.S. Pat. No. 5,162,410 that the adhesive compositions described therein would possess utility in the personal care arena.

SUMMARY OF THE INVENTION

The invention relates to a method of enhancing the adherence to the skin or eyelash of a personal care preparation containing an active ingredient. The method involves incorporating into the skin care preparation a film forming agent as an ingredient thereof, and applying the skin care preparation containing the active ingredient and the film forming agent to the skin. The film forming agent according to the present invention is a silicone pressure sensitive adhesive.

The invention further relates to a sunscreen preparation containing a film forming agent and at least one ultraviolet light absorbing compound as an active ingredient. The improvement resides in the use of a silicone pressure sensitive adhesive as the film forming agent in the sunscreen preparation.

In addition, the invention relates to an eye cosmetic containing a film forming agent, a pigment, a wax, an oil, and a preservative. Again, the improvement resides in the use of a silicone pressure sensitive adhesive as the film forming agent in the eye cosmetic to adhere the active ingredient to the eyelashes.

These and other features, objects, and advantages, of the herein described present invention will become more apparent from a consideration of the following detailed description thereof.

DETAILED DESCRIPTION OF THE INVENTION

The film forming agent employed in accordance with the present invention is a non-flammable hot-melt silicone pressure sensitive adhesive composition comprising a mixture of:

(i) 40 to 70 parts by weight of a trimethylsilyl-endblocked low molecular weight hydrocarbon or benzene-soluble resinous copolymer containing silicon bonded hydroxyl radicals and consisting essentially of triorganosiloxy units of the formula $R''''_3SiO_{\frac{1}{2}}$ and tetrafunctional siloxy units of the formula $SiO_{4/2}$ in a ratio of 0.6 to 0.9 triorganosiloxy units per tetrafunctional siloxy unit present in the copolymer molecule, and $R''''$ is a monovalent hydrocarbon radical of one to six carbon atoms;

(ii) 30 to 60 parts by weight of a silanol-endblocked polydiorganosiloxane fluid, wherein the total parts by weight of the resinous copolymer and the silanol-endblocked polydiorganosiloxane fluid equals 100 parts; the mixture of ( i ) and ( ii ) exhibiting tackiness and adhesiveness, and blended with:

(iii) 0.5 to 20 weight percent, based on the total weight of the resinous copolymer and the silanol-endblocked polydiorganosiloxane fluid, of a phenyl-containing polysiloxane fluid of the formula $A_3SiO[Si(C_6H_5)(R'O)]_x[Si(R_2O)]_ySiB_3$ wherein R is a monovalent radical selected from the group consisting of $-OSiR''_3$, hydrocarbon radicals of one to three carbon atoms, and $-OH$; R' is a monovalent radical selected from the group consisting of $-OSiR''_3$, $-OH$ and $-CH_3$; R'' is a monovalent hydrocarbon radical of one to three carbon atoms; A and B are endblocking units selected from the group consisting of $-OSiR'''_3$ where R''' is a hydrocarbon radical of one to eight carbon atoms, $-OH$, halide radicals, and amine radicals; x is an integer having a value greater than zero; and the value of x and y is such that the phenyl-containing polysiloxane fluid has a viscosity at twenty-five degrees Centigrade of 5 to 60,000 centistokes, and has 1 to 100 phenyl groups per 100 siloxane units.

Details of the adhesive and examples of a process for its manufacture are set forth in U.S. Pat. No. 5,162,410 noted previously, and reference may be had thereto. The adhesive is available commercially from Dow Corning Corporation, Midland, Mich., USA.

For the purpose of illustrating the present invention in more detail, oil in water emulsion mascara compositions B-H were prepared containing the adhesive, and these compositions are set forth in Table I. Mascara composition H was used as the control mascara. The various ingredients of the mascara compositions are arranged as Groups A-E as indicated in Table I.

TABLE I

| INGREDIENTS | MASCARA COMPOSITIONS (WEIGHT %) | | | | | | |
| --- | --- | --- | --- | --- | --- | --- | --- |
|  | B | C | D | E | F | G | H |
| Group A: |  |  |  |  |  |  |  |
| 1. Water | 47.5 | 57.5 | 57.5 | 57.5 | 47.5 | 47.5 | 57.5 |
| 2. Magnesium Aluminum Silicate | 1.5 | 1.5 | 1.5 | 1.5 | 1.5 | 1.5 | 1.5 |
| 3. Triethonolamine | 2.0 | 2.0 | 2.0 | 2.0 | 2.0 | 2.0 | 2.0 |

TABLE I-continued

| INGREDIENTS | MASCARA COMPOSITIONS (WEIGHT %) | | | | | | |
| --- | --- | --- | --- | --- | --- | --- | --- |
| | B | C | D | E | F | G | H |
| Group B: | | | | | | | |
| 4. Black Iron Oxide | 10.0 | 10.0 | 10.0 | 10.0 | 10.0 | 10.0 | 10.0 |
| 5. Ultramarine Blue | 2.0 | 2.0 | 2.0 | 2.0 | 2.0 | 2.0 | 2.0 |
| Group C: | | | | | | | |
| 6. Carnauba Wax | 2.0 | 2.0 | 2.0 | 2.0 | 2.0 | 2.0 | 2.0 |
| 7. Candelilla Wax | 5.0 | 5.0 | 5.0 | 5.0 | 5.0 | 5.0 | 5.0 |
| 8. Stearic Acid | 4.0 | 4.0 | 4.0 | 4.0 | 4.0 | 4.0 | 4.0 |
| 9. Beeswax | 5.0 | — | — | — | 5.0 | 5.0 | 5.0 |
| 10. Petroleum Distillate (ISOPAR ®) | 10.0 | 10.0 | 10.0 | 10.0 | 10.0 | 10 0 | 10.0 |
| 11A. Alkylmethyl Silicone Wax with C$_{30}$+ alkyl group | — | 5.0 | — | — | — | — | — |
| 11B. Sample as 11A but shorter silicone backbone | — | — | 5.0 | — | — | — | — |
| 11C. Same as 11A but with C$_{22-24}$ alkyl group | — | — | — | 5.0 | — | — | — |
| Group D: | | | | | | | |
| 12A. Aqueous Silicone Latex | 10.0 | — | — | — | — | — | — |
| 12B. Silicone Pressure Sensitive Adhesive | — | — | — | — | 10.0 | — | — |
| 12C. High Molecular Weight Silicone Gum HOMe$_2$SiO(Me$_2$SiO)$_n$SiMe$_2$OH | — | — | — | — | — | 10.0 | — |
| Group E: | | | | | | | |
| 13. Diazolidinyl urea (Germaben ® II-E) | 1.0 | 1.0 | 1.0 | 1.0 | 1.0 | 1.0 | 1.0 |

In Table I, ingredient 2 of Group A is a thickener sold under the trademark VEEGUM ® by R. T. Vanderbilt Co. Inc., of Norwalk, Conn. The petroleum distillate shown as ingredient 10 of Group C is a mixture of isoparaffins containing hydrocarbons having ten to twelve carbon atoms, sold under the trademark ISOPAR ® L by the Exxon Chemical Company, Houston, Tex. The preservative GERMABEN ® II-E shown as ingredient 13 in Group E, is a product and a trademark of Sutton Laboratories of Chatham, N.J.

The silicone pressure sensitive adhesive used as the film forming agent in the mascara compositions in Table I appears in Group D as ingredient 12B.

In Table I, an "in situ" emulsifier is employed in the form of the compound triethanolamine stearate which is formed by the combination of triethanolamine (Ingredient 3) and stearic acid ( Ingredient 8 ).

EXAMPLE I

Mascara compositions B-H in the form of oil in water emulsions were prepared by heating ingredient 1 and adding ingredients 2, and 3, in that order. The mixture of ingredients 1-3 was covered and heated to eighty-five degrees Centigrade. The pigment ingredients 4 and 5 of Group B were added to the ingredients 1-3 of Group A and dispersed using a homomixer. The ingredients of Groups A and B were maintained at eighty-five degrees Centigrade. All of the ingredients of Group C were heated together to eighty degrees Centigrade and added to Groups A and B using a propeller mixer. Groups A, B, and C, were mixed at eighty degrees Centigrade for fifteen minutes, cooled to fifty degrees Centigrade, and the ingredients of Group D were added. Groups A, B, C, and D, were cooled to thirty-five degrees Centigrade and the preservative of Group E was added, The mascara compositions were filled into vials and evaluated in Examples II and III.

EXAMPLE II

The mascara compositions in Table I were evaluated for shelf stability, and found to be stable at temperatures of forty and forty-five degrees Centigrade after a period of six months.

EXAMPLE III

Mascara compositions B-H in Table I were evaluated in vivo by volunteers. The volunteers applied the mascara compositions to their eyelashes and attempted to wash off the mascara. Each mascara composition was evaluated on the basis of its difficulty to wash off the eye lashes using water, as well as soap and water. The volunteers reported that mascara composition F which is representative of the present invention, was one of the most difficult to wash off.

In the tests, Composition F was evaluated against other compositions containing other types of silicone film forming materials shown as ingredients 11A-11C, 12A, and 12C, in Table I. Ingredient 11A was an alkylmethyl functional silicone wax containing an alkyl group of about thirty carbon atoms. Ingredient 11B was an alkylmethyl functional silicone wax containing an alkyl group of about thirty carbon atoms, and differed from silicone wax 11A only in the length of the siloxane backbone. The siloxane backbone of wax 11B was shorter than the siloxane backbone of was 11A. Ingredient 11C was also an alkylmethyl functional silicone wax similar to silicone wax 11A, but wax 11C contained an alkyl group of about 22-24 carbon atoms. Ingredient 12C was a high molecular weight silicone gum having the formula HOMe$_2$SiO(Me$_2$SiO)$_n$SiMe$_2$OH in which Me is methyl and n is an integer having a value of about ten thousand.

The film forming silicone Ingredient 12A was an aqueous latex of a crosslinked polydiorganosiloxane prepared by a method consisting essentially of:

(A) homogenizing a mixture consisting essentially of (1) one hundred parts by weight of polydiorganosiloxane of the formula HO(R$_2$SiO)$_x$H wherein R is a radical selected from the group consisting of methyl, ethyl, propyl, phenyl, vinyl, allyl, and 3,3,3-trifluoropropyl, and x is an integer having an average value of three to one hundred; (2) 15-75 millimoles of surface active anionic catalyst per kilogram of polydiorganosiloxane wherein said catalyst is selected from the group consisting of dodecylbenzene sulfonic acid and hydrogen lauryl sulfate; and (3) water, to yield an oil in water emulsion;

(B) admixing 0.5-15 parts by weight of an alkoxy silicon compound selected from the group consisting of (i) silanes of the formula $R'_a Si(OR^3)_{4-a}$ wherein $R'$ is a monovalent hydrocarbon radical having up to twelve carbon atoms, $R^3$ is an alkyl radical having one to six carbon atoms, and $a$ has a value of zero or one; (ii) a partial hydrolyzate of the silane which is soluble in the polydiorganosiloxane; and (iii) mixtures of the silane and the partial hydrolyzate;

(C) maintaining the emulsion at a temperature of fifteen to thirty degrees Centigrade for at least five hours at a pH of less than five until a crosslinked polymer emulsion is formed;

(D) admixing sufficient base to raise the pH of the crosslinked polymer emulsion to greater than seven; and optionally (E) admixing greater than one part by weight of collodial silica sol or colloidal silsesquioxane) to yield a latex which produces an elastomer upon removal of the water at room temperature.

Details of the aqueous latex and examples of a process for its manufacture are set forth in U.S. Pat. No. 4,584,341 issued Apr. 22, 1986, which is incorporated herein by reference, and reference may be had thereto. The aqueous latex is available commercially from Dow Corning Corporation, Midland, Mich. USA.

The testing results reported by the volunteers were confirmed by independent testing of mascara composition F against other mascaras containing organic film forming agents such as polyvinylpyrrolidone and acrylate based polymers.

While Examples I-III and Table I are directed to mascara compositions in the form of oil in water emulsions, water in oil emulsions may be formulated as well. Further, the silicone pressure sensitive adhesive may be used in the preparation of other pigmented eye cosmetic preparations such as eyebrow pencils and liquids, eye shadow, eyeliner, and eye cream. In addition, it is contemplated that mascara compositions containing the adhesive as the film forming agent may be formulated as cake or block mascara, liquid mascara, or cream mascara products, as well as solvent compatible compositions, and anhydrous preparations.

Waxes which may be employed in preparing mascara compositions in accordance with the present invention include carnauba, beewax, ceresin, paraffin, candelilla, bayberry, montan, spermaceti, castor wax, ozokerite, Fisher-Tropsch waxes, and microcrystalline waxes. Suitable oils include castor oil, olive oil, jojoba oil, stearic acid, lanolin alcohols, paraffin oil, and silicone oils. Examples of pigments include iron oxide, titanium oxide, ultramarine, chromium oxide, carbon black, and any of the United States Government Food & Drug Administration (FDA) certified organic dyes and lakes. Preservatives include methyl paraben, propyl paraben, butyl paraben, diazolidinyl urea, and imidazolidinyl urea.

It may be desirable to incorporate in the mascara composition other conventional ingredients such as emulsifiers and surfactants; humectants such as glycerine; perfumes; sunscreen compounds; vitamins; hormones; amino acids; antioxidants such as propyl, octyl, and dodecyl, esters of gallic acid, butylated hydroxyanisole, butylated hydroxytoluene, and nordihydroguaiaretic acid; extenders such as talc, mica, kaolin, and cericite; feel modifiers such as organic esters and silicone fluids; opacifiers such as titanium dioxide and fatty alcohols; fragrances; and solvents such as ethanol, isopropanol, and volatile silicones such as hexamethyldisiloxane and octamethylcyclotetrasiloxane.

A mascara formulation in accordance with the present invention will preferably contain 5-20 percent by weight, or most preferably about ten percent by weight, of the silicone pressure sensitive adhesive; 20-60 percent by weight, or most preferably about 30-50 percent by weight, of water; 4-10 percent by weight of a wax or a mixture of waxes; 10-20 percent by weight of one or more pigments; one percent by weight or less of a preservative; 5-15 percent by weight of one or more surfactants or emulsifiers; 0.2-3.0 percent by weight of a thickener; zero to one percent by weight of a feel modifier; and 1-4 percent by weight of an opacifier.

The concept of the present invention is further illustrated by reference to Table II which shows five (5) sunscreen compositions A-E which were prepared. The various ingredients of the sunscreen compositions A-E are grouped as Phases A, B, and C. Ingredients in Table II which correspond to ingredients in Table I above are similarly identified. Any differences are noted below.

TABLE II

| | INGREDIENTS | SUNSCREEN COMPOSITIONS (WEIGHT PERCENT) | | | | |
|---|---|---|---|---|---|---|
| | | A | B | C | D | E |
| PHASE A: | | | | | | |
| 1. | Water | 68.21 | 63.21 | 70.71 | 68.57 | 70.71 |
| 2. | Polyacrylate (CARBOPOL ® 940) | 0.14 | 0.14 | 0.14 | 0.14 | 0.14 |
| 3. | GLYCERIN | 2.50 | 2.50 | 2.50 | 2.50 | 2.50 |
| 4. | Methyl Paraben | 0.15 | 0.15 | 0.15 | 0.15 | 0.15 |
| 5. | Triethanolamine | 1.40 | 1.40 | 1.40 | 1.40 | 1.40 |
| PHASE B: | | | | | | |
| 6. | Stearic Acid | 4.00 | 4.00 | 4.00 | 4.00 | 4.00 |
| 7. | Cetyl Alcohol | 1.00 | 1.00 | 1.00 | 1.00 | 1.00 |
| 8. | DEA-Cetyl Phosphate (AMPHISOL) | 1.00 | 1.00 | 1.00 | 1.00 | 1.00 |
| 9. | Propyl Parabene | 0.10 | 0.10 | 0.10 | 0.10 | 0.10 |
| PHASE C: | | | | | | |
| 10. | $C_{12}$-$C_{15}$ Alkylbenzoate (FINSOLV ® TN) | 4.00 | 4.00 | 4.00 | 4.00 | 4.00 |
| 11. | 2-ethylhexyl-p-methoxycinnimate PARSOL ® MCX | 7.00 | 7.00 | 7.00 | 7.00 | 7.00 |
| 12. | 2-hydroxy-4-methoxybenzophenone UVINUL ® M-40 | 3.00 | 5.00 | 3.00 | 3.00 | 3.00 |
| 13A. | Silicone Pressure Sensitive Adhesive | 7.50 | — | — | — | — |
| 13B. | Acrylates Polymer POLYTRAP ® | — | 12.50 | — | — | — |
| 13C. | Silicone Polymer | — | — | 5.00 | — | — |
| 13D. | Crosslinked Cationic Emulsion of Polydimethylsiloxane | — | — | — | 7.14 | — |
| 13E. | Aqueous Silicone Latex | — | — | — | — | 5.00 |

Thus, in Table II, the polyacrylate thickener CARBOPOL ® 940 in Phase A is a product and trademark of the B. F. Goodrich Company of Cleveland, Ohio. Glycerin was present in Phase A as a humectant. The anionic surfactant AMPHISOL in Phase B is a trademark and a product of Givaudan Corporation, Clifton, N.J. Cetyl alcohol was present in Phase B as an opacifier. The solubilizer FINSOLV® TN in Phase C is a product and a trademark of Finetax Incorporated of Elmwood Park, N.J.. The sunscreen compound PARSOL® MCX in Phase C is a product and a trademark of Givaudan Corporation of Clifton, N.J.. The sunscreen compound UVINUL® M-40 in Phase C is a product and a trademark of BASF Corporation of Parsippany, N.J.

The acrylates polymer POLYTRAP® in Phase C is a product and trademark of the Dow Corning Corporation, Midland, Mich. POLYTRAP® is a micron sized powder of macroporous particulates and is described in various patents including U.S. Pat. No. 33429 issued Nov. 6, 1990, and U.S. Pat. No. 5,035,890 issued Jul. 30, 1991. The silicone polymer 13C was a dimethylvinyl endblocked trifluoropropylmethyl siloxane polymer. The silicone ingredient 13D was a water thin white emulsion which had a silicone content of about thirty-five percent by weight in water, and a pH of six.

EXAMPLE IV

Sunscreen compositions A-E in Table II were prepared by mixing together the ingredients of Phase A, and heating the mixture to seventy-six degrees Centigrade. The ingredients of Phase B were mixed together in order, and heated to seventy-five degrees Centigrade. Phase B was added to Phase A, and the temperature was maintained. Ingredients 10-12 of Phase C were mixed together in order and heated until dissolved. This portion of Phase C was added to ingredient 13A-E as appropriate, and all of Phase C was added to Phases A and B at fifty degrees Centigrade. The sunscreen compositions were stirred until a temperature of forty degrees Centigrade was reached, and filled into vials for evaluation.

EXAMPLE V

Sunscreen compositions A-E were evaluated in vivo by volunteers. The amount of sunscreen composition remaining on the skin after eighty minutes of soaking was determined by Fourier-Transform Infrared Spectroscopy (FTIR). The sunscreen compositions A-E were evaluated against a commercial sunscreen product containing a GANEX® resin as the film forming agent. GANEX® is a polyvinylpyrrolidone based polymer commonly used in consumer sunscreen products, and is a product and trademark of International Specialty Products of Wayne, N.J.. It was determined that the sunscreen composition A of the present invention was one of the best performers against GANEX®. Slightly more than thirty-five percent of the sunscreen composition A which contained the adhesive remained on the skin. By comparison, only thirty percent of the sunscreen containing GANEX® as the film forming agent remained on the skin.

Sunscreen compositions according to the present invention may be formulated as oils, lotions, creams, or gels.

In those instances where a composition is in the form of an oil in water emulsion or a water in oil emulsion, one or more surfactants may be required. Suitable surfactants would include one or more of the various categories of silicon-free organic emulsifiers. These emulsifiers, it is noted, may be used in combination with certain polydiorganosiloxane-polyoxyalkylene copolymers, as explained in detail in U.S. Pat. No. 4,122,029 issued Oct. 24, 1978, and in U.S. Pat. No. 4,311,695 issued Jan. 19, 1982.

Sunscreen agents according to the invention are used in amounts which are within the restricted limits or less, as established by the US Government Food & Drug Administration. Representative sunscreen agents or mixtures of such agents which may be used in the preparation of the compositions of the invention include 4-aminobenzoic acid; homomethyl salicylate; 2-hydroxy-4-methoxy benzophenone; 2-phenylbenzimidazol-5-sulfonic acid; 4-dimethyl amino benzoic acid-2-ethylhexyl ester; 4-methoxy cinnamic acid isoamyl ester; 4-methoxy cinnamic acid-2-ethylhexyl ester; 3-(4'-methyl) benzylidine-bornane-2-one; 1-(4'-isopropylphenyl )-3-phenyl-1-propane-1,3-diode; and 1-(4'-t-butylphenyl)-3-(4-methoxyphenyl)-propane-1,3-dioxide.

Among the various moisturizing oils which may be used in order to formulate sunscreen compositions are mineral oil, peanut oil, sesame oil, avocado oil, coconut oil, cocoa butter, almond oil, safflower oil, corn oil, and cotton seed oil. Other oils may be added for the purpose of improving the spreadability of the sunscreen composition such as silicone fluids; and fatty acid esters such as isopropyl myristate, isopropyl palmitate, isopropyl stearate, butyl stearate, and cetyl stearate. Other conventional adjuvants necessary to produce acceptable consumer sunscreen products may be included in the compositions such as antioxidants, preservatives, fragrances and perfumes, emulsifiers, humectants, and solvents.

A sunscreen formulation in accordance with the present invention will preferably contain 5-20 percent by weight, or most preferably about ten percent by weight, of the silicone pressure sensitive adhesive; 20-60 percent by weight, or most preferably about 30-50 percent by weight, of water; one percent by weight or less of a preservative; 4-8 percent by weight of one or more surfactants or emulsifiers; 0.1-2.0 percent by weight of a thickener; zero to five percent by weight of a feel modifier; 0.2-1.0 percent by weight of a fragrance; and 1-4 percent by an opacifier.

The cosmetic compositions set forth above in Tables I and II and in Examples I-V, when applied to the skin, leave a flexible and stretchable film on the surface of the skin. Therefore, active ingredients included in these cosmetic products such as sunscreen compounds for example, will tend to be bound in the flexible film, and will remain in place on the skin significantly longer, despite sweating, swimming, and exercise. Further, the compositions exhibit improved physical resistance and hence are physically difficult to rub off from the skin. These obvious advantages of the compositions according to the present invention can be attributed to the presence in the compositions of the silicone pressure sensitive adhesive.

Non-volatile silicone fluids which may be used in the preparation of the compositions of the present invention are organic polysiloxanes having a viscosity in the range of about 5 to as high as several million centistokes, preferably about 100 to about 10,000 centistokes. A mixture of polysiloxanes having relatively higher and relatively lower viscosities can employed. Such polysiloxanes have the repeating unit

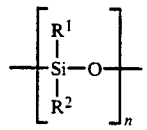

wherein n is an integer having a value greater than 1; $R^1$ and $R^2$ are alkyl radicals of one to seven carbon atoms, or a phenyl group; and $R^1$ and $R^2$ may be the same or different. Illustrative polysiloxanes are polydimethylsiloxane, polydiethylsiloxane, polymethylethylsiloxane, polymethylphenylsiloxane, polydiphenylsiloxanes, and copolymers of two or more of the foregoing siloxanes.

In some instances it may be desirable to include a volatile silicone fluid in the compositions of the present invention. Suitable fluids are low viscosity methylsilicone fluids. The volatile low viscosity methylsilicone fluid corresponds to the average unit formula $(CH_3)_aSiO_{(4-a/2)}$ wherein a is an integer having an average value of from two to three.

The methylsilicone fluid contains siloxane units joined by Si-O-Si bonds. Representative units are $(CH_3)_3SiO_{1/8}$, $(CH_3)_2SiO_{2/2}$, $(CH_3)SiO_{3/2}$, and $SiO_{4/2}$. These units are present in molar amounts such that there is provided an average of from about two to three methyl groups per silicon atom in the methylsilicone fluid, whereby the methylsilicone fluid has a viscosity of less than about one hundred centistokes measured at twenty-five degrees Centigrade.

The volatile low viscosity methylsilicone fluid contains dimethylsiloxane units and optionally trimethylsiloxane units. Preferably, the methylsilicone fluid has a viscosity of less than about ten centistokes. Representative compounds are cyclopolysiloxane compounds of the general formula $[(CH_3)_2SiO]_x$, and linear siloxane compounds of the general formula $(CH_3)_3SiO[(CH_3)_2SiO]_ySi(CH_3)_3$, in which x is an integer having a value of from three to ten, and y is an integer having a value of from zero to about four.

The volatile low viscosity methylsilicones have boiling points generally less than about two hundred-fifty degrees Centigrade, and possess viscosities preferably generally less than about ten centistokes measured at twenty-five degrees Centigrade. Most preferably, the viscosity is 0.65 to 5.0 centistokes. The cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in accordance with the present invention are hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; and decamethylcyclopentasiloxane which has a boiling point of 205 degrees Centigrade and the formula $[(Me_2)SiO]_5$.

These methylsilicone fluids may be used alone, or as mixtures in combinations of two or more. Mixtures of the methylsilicone fluids will result in a volatile material having an evaporating behavior different from any one of the individual methylsilicone fluids. The methylsilicone fluids and methods for their preparation are known in the art, and such fluids are commercially available.

In some instances, it may be desirable to replace one or more of the methyl groups in the methylsilicone fluid with other groups. Thus, there may be substituted groups such as alkyl radicals having two to twelve carbon atoms; aryl radicals having six to ten carbon atoms; amine groups; vinyl; hydroxyl; haloalkyl groups; aralkyl groups; and acrylate groups, for example.

The compositions of this invention may contain a surfactant such as an anionic and amphoteric surfactant. Suitable anionic surfactants include sulfonated and sulfated alkyl, aralkyl and alkaryl anionic surfactants; alkyl succinates; alkyl sulfosuccinates and N-alkyl sarcosinates. Representative surfactants are the sodium, magnesium, ammonium, and the mono-, di- and triethanolamine salts of alkyl and aralkyl sulfates as well as the salts of alkaryl sulfonates. The alkyl groups of the surfactants generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic surfactants include, among others, sodium lauryl sulfate, sodium lauryl ether sulfate, ammonium lauryl sulfate, triethanolamine lauryl sulfate, sodium C14-16 olefin sulfonate, ammonium pareth-25 sulfate (ammonium salt of a sulfated polyethylene glycol ether of a mixture of synthetic C12-15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate. Organic compounds of phosphoric acid may also be used such as diethanolamine salts of cetyl phosphate, one of which is DEA-Cetyl Phosphate.

Surfactants generally classified as amphoteric or ampholytic include cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine.

Other suitable amphoteric surfactants include the quaternary cycloimidates, betaines, and sultaines disclosed in U.S. Pat. No. 3,964,500.

The betaines may have the structure:

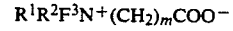

wherein $R^1$ is an alkyl group having about 12 to 18 carbon atoms or a mixture thereof, $R^2$ and $R^3$ are independently lower alkyl groups having 1 to 3 carbon atoms, and m is an integer from 1 to 4. Specific betaines are alpha-( tetradecyldimethylammonio )acetate, beta- (hexadecyldiethylammonio)propionate, and gamma-(dodecyldimethylammonio) butyrate.

The sultaines may have the structure:

$$R^1R^2R^3N^+(CH_2)_mSO_3^-$$

wherein $R^1$ $R^2$ $R^3$ and m are defined as above Specific useful sultaines are 3-(dodecyldimethylammonio)-propane-1-sulfonate, and 3-( tetradecyldimethylammonio)ethane-1-sulfonate.

The compositions of this invention may contain a nonionic surfactant which is a fatty acid alkanolamide or amine oxide surfactant. The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, fatty acid diethanolamides such as isostearic acid diethanolamide, lauric acid diethanolamide, capric acid diethanolamide, coconut fatty acid diethanolamide linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanolamide and lauric acid monoisopropanolamide.

The amine oxides are known nonionic surfactants obtained by oxidizing a tertiary amine to form the amine oxide. They are sometimes referred to as polar nonionic surfactants. Amine oxide surfactants include, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxy-propylamine oxide. The hydrophobic portion of the amine oxide surfactants is generally provided by a fatty hydrocarbon chain containing from 10 to 21 carbon atoms. Representative surfactants include lauric acid diethanolamide, N-lauryl dimethylamine oxide, coconut acid diethanolamide, myristic acid diethanolamide, and oleic acid diethanolamide.

Additional categories of surfactants may be included such as cationic and zwitterionic surfactants, and representative compounds are set forth in detail in U.S. Pat. No. 4,902,499, issued Feb. 20, 1990.

Suitable thickeners which may be employed are sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as sodium or ammonium chloride, saccharides such as fructose and glucose, and derivatives of saccharides such as PEG-120 methyl glucose dioleate.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. An eye cosmetic comprising a film forming agent, a pigment, a wax, and an oil, the film forming agent being a non-flammable hot-melt silicone pressure sensitive adhesive composition comprising a mixture of:
   (i) 40 to 70 parts by weight of a trimethylsilyl-endblocked benzene-soluble resinous copolymer containing silicon bonded hydroxyl radicals and consisting essentially of triorganosiloxy units of the formula $R'''_3SiO_{\frac{1}{2}}$ and tetrafunctional siloxy units of the formula $SiO_{4/2}$ in a ratio of 0.6 to 0.9 triorganosiloxy units per tetrafunctional siloxy unit present in the copolymer molecule, and $R'''$ is a monovalent hydrocarbon radical of one to six carbon atoms;
   (ii) 30 to 60 parts by weight of a silanol-endblocked polydiorganosiloxane fluid, wherein the total parts by weight of the resinous copolymer and the silanol-endblocked polydiorganosiloxane fluid equals 100 parts; the mixture of ( i ) and ( ii ) exhibiting tackiness and adhesiveness, and blended with: (iii) 0.5 to 20 weight percent, based on the total weight of the resinous copolymer and the silanol-endblocked polydiorganosiloxane fluid, of a phenyl-containing polysiloxane fluid of the formula $A_3SiO[Si(C_6H_5)(R')O]_x[Si(R_2)O]_ySiB_3$ wherein R is a monovalent radical selected from the group consisting of $-OSiR''_3$, hydrocarbon radicals of one to three carbon atoms, and $-OH$; $R'$ is a monovalent radical selected from the group consisting of $-OSiR''_3$, $-OH$ and $-CH_3$; $R''$ is a monovalent hydrocarbon radical of one to three carbon atoms; A and B are endblocking units selected from the group consisting of $-OSiR'''_3$ where $R'''$ is a hydrocarbon radical of one to eight carbon atoms, $-OH$, halide radicals, and amine radicals; x is an integer having a value greater than zero; and the value of x and y is such that the phenyl-containing polysiloxane fluid has a viscosity at twenty-five degrees Centigrade of 5 to 60,000 centistokes, and has 1 to 100 phenyl groups per 100 siloxane units.

2. The eye cosmetic according to claim 1 which the film forming agent is present in the amount of about 5-20 percent by weight.

* * * * *